(12) United States Patent
Henry (10) Patent No.: US 8,726,722 B2
(45) Date of Patent: May 20, 2014

(54) DETERMINING CONCENTRATIONS OF COMPONENTS OF A MIXTURE

(75) Inventor: Manus Henry, Oxford (GB)

(73) Assignee: Invensys Systems, Inc., Foxboro, MA (US)

( * ) Notice: Subject to any disclaimer, the term of this patent is extended or adjusted under 35 U.S.C. 154(b) by 296 days.

(21) Appl. No.: 13/302,780

(22) Filed: Nov. 22, 2011

(65) Prior Publication Data

US 2012/0137754 A1 Jun. 7, 2012

Related U.S. Application Data

(60) Provisional application No. 61/418,659, filed on Dec. 1, 2010.

(51) Int. Cl.
*G01N 11/02* (2006.01)
*G01N 11/00* (2006.01)

(52) U.S. Cl.
USPC ........ 73/61.44; 73/61.43; 73/61.41; 73/53.01

(58) Field of Classification Search
USPC ..................... 73/61.44, 61.43, 61.41, 53.01
See application file for complete search history.

(56) References Cited

U.S. PATENT DOCUMENTS

| | | | |
|---|---|---|---|
| 3,653,835 A | 4/1972 | Brandel | |
| 4,009,998 A | 3/1977 | Benningfield, Jr. | |
| 5,583,049 A | 12/1996 | Altman et al. | |
| 5,583,275 A | 12/1996 | Kranz et al. | |
| 5,751,415 A | 5/1998 | Smith et al. | |
| 6,096,553 A | 8/2000 | Heald et al. | |
| 6,134,951 A | 10/2000 | Scott et al. | |
| 2010/0023275 A1 | 1/2010 | Trygstad | |

FOREIGN PATENT DOCUMENTS

EP   1720013 A2   11/2006

OTHER PUBLICATIONS

International Search Report from International Application No. PCT/US2009/051764, dated Oct. 30, 2009, 2 pages.
Friedman, Y. "Engineering Models for Inferential Controls." Process Optimization Conference. Marriott Houston Westside, Houston, Texas Apr. 7-10, 1997, by Gulf Publishing Company and Hydrocarbon Processing (online), retrieved from http://petrocontrol.com/pdf1997_Eng_models.pdf, 20 pages.
SpectrOn NIR Refinery Monitor, Datasheet (online), Guided wave, Inc. (2006), retrieved from http://web.archive.org/web20061129021719/http://www.guided-wave.com/products/spectrometers/spectron_refinery_monitor/, 6 pages.
European Search Report for related European Application No. 11191568.2 dated May 21, 2012, 8 pgs.

*Primary Examiner* — Christine T Mui
(74) *Attorney, Agent, or Firm* — Edward S. Jarmolowicz, Esq.

(57) ABSTRACT

Systems and methods for determining concentrations of components of a multiphase fluid. A first flowmeter receives a fluid flow and generates measurements of the fluid flow. After at least partially separating the fluid flow into mixtures of its components, second and third flowmeters generate measurements of the mixtures. A data processing apparatus operatively coupled to the flowmeters receives the measurements and determines concentrations of the components of the fluid flow. In an embodiment, the measurements are mass flow and density readings.

26 Claims, 4 Drawing Sheets

DETERMINING CONCENTRATIONS OF COMPONENTS OF A MIXTURE

CROSS REFERENCE TO RELATED APPLICATIONS

This application claims the benefit of U.S. Provisional Application Ser. No. 61/418,659 entitled "Determining Concentrations of Components of a Mixture" filed Dec. 1, 2010, the contents of which are expressly incorporated herein by reference in their entirety including the contents and teachings of any references contained therein. In addition, this application relates to U.S. application Ser. No. 12/509,212 entitled "System and Method for Alkylation Process Analysis" filed Jul. 24, 2009, which claims the benefit of U.S. Provisional Application Ser. No. 61/084,142 entitled "Multi-Property Measurement" filed Jul. 28, 2008, relates to U.S. application Ser. No. 12/905,559 entitled "System and Method for Alkylation Process Analysis" filed Oct. 15, 2010, which is a Continuation-in-Part of U.S. application Ser. No. 12/720,533 entitled "System and Method for Alkylation Process Analysis" filed Mar. 9, 2010 (now U.S. Pat. No. 7,972,863), which is a Continuation-in-Part of U.S. application Ser. No. 12/509,212, and relates to U.S. application Ser. No. 13/111,448 entitled "System and Method for Alkylation Process Analysis" filed May 19, 2011, which is a Continuation of U.S. application Ser. No. 12/720,533, the contents of which are expressly incorporated herein by reference in their entirety including the contents and teachings of any references contained therein.

TECHNICAL FIELD

This document relates to determining concentrations of components in a multiphase flow.

BACKGROUND

Many industrial processes involve a mixture of a number of different fluids having different properties, for example, density or concentration. In some cases, knowing the concentration of the components of the mixture is useful for controlling the process. For example, the synthesis of isooctane (i.e., octane) for blending in a dynamic gasoline pool is a step in petroleum refining. One process for producing octane is HF Alkylation. In this process, Hydrogen Fluoride (HF, hydrofluoric acid) serves as a catalyst for the reaction of isobutane and $C_4$ olefins to form octane or "alkylate." A catalyst is a substance that increases a rate of a chemical reaction without being consumed in the process. The alkylation process turns low-molecular weight hydrocarbons, which formerly were waste, into a component of gasoline.

HF catalyst includes three components—HF (approximately 90%), water (approximately 1%), and acid-soluble organics (ASO) as the remainder. The concentration of each of the components affects the alkylation process. For example, a small concentration of water improves reaction efficiency, whereas a large concentration increases corrosiveness of the catalyst. Further, the concentration of HF can affect its role as a catalyst. For example, in acid runaway, HF's role as a catalyst is compromised when the HF concentration falls below a threshold concentration and begins to participate as a reactant in side reactions that consume HF, but do not produce octane.

Acid runaway can be avoided by knowing HF and ASO concentrations. In particular, to avoid acid runaway, an HF concentration margin can be maintained over the critical concentration. Uncertainty around the HF and ASO concentrations can necessitate a greater margin over the critical concentration and cause a decrease in efficiency. In general, to optimize the alkylation process, the concentrations of the components of the HF catalyst are controlled. Minimizing a net consumption of HF by fine-tuning the operation of the alkylation unit can increase safety and profitability of the unit. For example, large output of octane barrels can be obtained at minimum cost by operating the unit at the lowest possible HF concentration without risking acid runaway. Grab-sampling extraction for laboratory analysis and online analysis are two methods for monitoring the concentrations of the components of HF catalyst (henceforth referred to as "HF mix").

SUMMARY

This document describes technologies related to determining the concentrations of components in a multiphase flow. For example, this document describes technologies relating to an acid catalyst analyzer that can determine concentrations of the components of a sample mix that includes isobutane and HF mix.

Particular implementations of the subject matter described in this document can be implemented so as to realize one or more of the following advantages. Knowing HF and ASO levels can allow operation of the HF rerun in a manner that optimizes octane barrels without the risk of acid runaway, leading to improvement in profitability and safety. By calculating, rather than estimating, a concentration of $iC_4$ in a sample volume that includes $iC_4$ and HF mix, the concentration of each component of the sample volume (i.e., $iC_4$, HF, ASO, and water) can be determined more accurately. The control systems implemented to control valve openings can enable a rapid, dynamic response to changes in the proportion of $iC_4$ in the sample stream. The instrumentation implemented to measure concentration and density can be simple—mere lengths of pipes—in comparison to other systems that can be used to perform similar operations, e.g., Fourier-Transform, Near-Infrared Spectroscopy (FTNIR) system. Encoding temperature corrections in the control feedback loop can decrease or eliminate the need to measure control sample temperature. When the system is a continuously flowing sample system, the need for a more complex sample handing system with frequently cycling shutoff valves can be negated. Consequently, the need for maintenance and periodic replacement of the valves can also be negated. The system can output diagnostic information—flow rate, pressure, and temperature—periodically.

The details of one or more implementations are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Methods, apparatuses, and systems for determining concentrations of components of a multiphase flow, for example, a mixture of HF mix and $iC_4$, are described below. In general, one or more flowmeters, one or more separation vessels, and one or more valves can be operated to separate one of the components (for example, $iC_4$) from the multiphase flow (for example, a mixture of HF mix and $iC_4$), and to determine the concentration of the components of the multiphase flow (for example, HF, ASO, water, and $iC_4$). For instance, readings from the flowmeters can be used to determine, rather than estimate, a concentration of each component of the multiphase flow. In some implementations, the position of a valve through which a component passes can be regulated such that noise in the readings taken by the flowmeters can be decreased or eliminated.

For example, in one implementation, a system receives a sample volume that includes a 4-component fluid that includes isobutane ($iC_4$) and HF mix (HF, water, and ASO). The sample volume flows through a first flowmeter into a separation vessel that separates the $iC_4$ from the HF mix. The HF mix is flowed through a second flowmeter and other instrumentation, and readings from the flowmeter and other instrumentation are used to determine the concentrations of the components of the HF mix. In particular, percentage concentrations of water, HF, and ASO are determined such that the sum of the percentage concentrations totals 100% for the HF mix. The $iC_4$ separated by the separation vessel is flowed from the separation vessel through a valve to a third flowmeter. The readings taken using the third flowmeter are used to determine a concentration of $iC_4$ flowing through the third flowmeter. As described below, the percentage concentration of each component of the HF mix is compared with the actual concentration of $iC_4$ in the sample volume to determine concentrations of each component in the sample volume. In an alternative or additional implementation, to maintain a balanced separation of the $iC_4$, a control feedback loop is implemented to control a position of the valve that controls the amount of $iC_4$, which has been separated by the separation vessel, that can flow through the third flowmeter, so that the third meter is filled only with $iC_4$, rather than a mixture of HF mix and $iC_4$. In this manner, the combined mass flowing through the second and third flowmeters may be kept, on average, equal to the mass flowing through the first flowmeter. This may decrease or eliminate noise in the readings taken by the third flowmeter, and further allow the direct measurement of the density of the $iC_4$.

Figure 1:
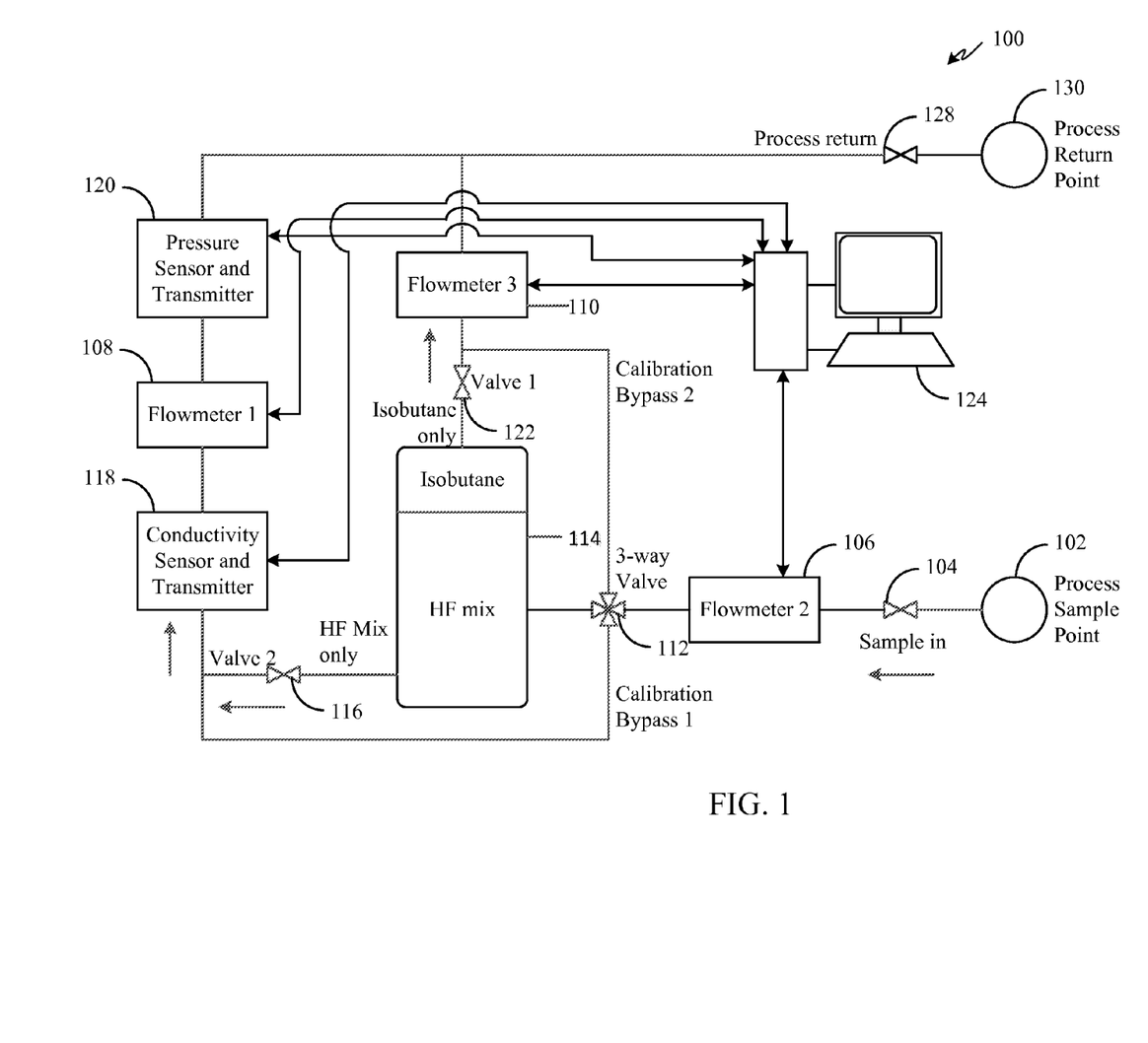
FIG. 1 is a diagram of an example of an acid catalyst analyzer system.

FIG. 1 is an example of an acid catalyst analyzer system 100. The system 100 is implemented to determine the concentrations of the components of a multiphase flow, for example, HF mix that includes HF, water, and ASO. In general, the system 100 samples a volume of a combination of HF mix and hydrocarbons (for example, isobutane, $iC_4$) from a process sample point 102 using a valve 104. The system 100 includes a first flowmeter 108, a second flowmeter 106, and a third flowmeter 110. Each of the flowmeters 106, 108, 110 can be a Coriolis flowmeter using a bent tube or a Coriolis flowmeter using a straight flowtube.

The sample volume, which is a combination of $iC_4$ and HF mix, is flowed through the second flowmeter 106. The $iC_4$ is in the sample volume because it is an input into the alkylation process. The system 100 includes a 3-way valve 112 that receives the flow from the second flowmeter 106. The valve 112 can be set in a first configuration to flow the HF mix and the $iC_4$ into a separation vessel 114 and in a second, separate configuration to cross-calibrate the three flowmeters. When the 3-way valve 112 is set in the first configuration, the sampled volume flows from the second flowmeter 106 into the separation vessel 114. The vessel 114 is sized to separate the HF mix from the $iC_4$ in the sampled volume based on a difference in the densities of the two fluids. Specifically, the HF mix and the $iC_4$ are immiscible; also, the density of $iC_4$ (approximately 600 $kg/m^3$) is less than that of the HF mix (approximately 1000 $kg/m^3$). The separation vessel 114 is sized such that the high density HF mix settles to a bottom region of the vessel 114 while the low density $iC_4$ rises to a top region of the vessel 114 due to the density difference. In some implementations, the separation vessel 114 is large relative to a diameter of the pipe that samples the volume from the process sample point 112. For example, each of a width of the separator vessel 114 and a height of the separator vessel 114 can be at least three times the diameter of the pipe that samples the volume.

Once the HF mix and the $iC_4$ have been separated, when the second valve 116 is open, pure HF mix (that includes HF, water, and ASO) flows through a conductivity sensor and transmitter 118, the first flowmeter 108, and a pressure sensor and transmitter 120, which collectively can measure parameters—conductivity, density, pressure, respectively—of the pure HF mix. Using readings from the pressure sensor 120, the conductivity sensor 118, and the first flowmeter 108, a computer system 124 (for example, a flow computer) can determine the concentration of HF, water, and ASO, respectively, in the HF mix. Specifically, the computer system 124 can determine a percentage concentration of water based on the conductivity sensor measurements and a percentage concentration of either HF or ASO from the first flowmeter 108 and pressure sensor 120 measurements. The computer system 124 can infer the concentration of either ASO or HF as a difference, from 100%, of the sum of the percentage concentrations of water and either HF or ASO. Notably, at this stage, the concentrations of HF, water, and ASO are determined as a percentage of the HF mix, and not that of the sample volume.

The separated $iC_4$ flows through the first valve 122. From the valve, the separated $iC_4$ stream flows through the third flowmeter 110, which takes density and mass flow rate readings of the $iC_4$. Based on the readings measured by the third flowmeter 110, the computer system 124 can determine a concentration of $iC_4$ in the sample volume. Having determined the concentration of $iC_4$, the computer system 124 can determine a concentration of HF mix in the sample volume, and then determine the concentration of each component of the HF mix in the sample volume. For example, if the percentage concentration of water in the HF mix is 1%, and the concentration of $iC_4$ in the sample is determined to be 7%, then the percentage concentration of HF mix in the sample is 93% (i.e., 100%-7%), and the percentage concentration of water in the sample volume is 0.93% (i.e. 1% of 93%). Similarly, if the percentage concentration of ASO and HF in the HF mix are 4% and 95%, respectively, then the percentage concentration of ASO and HF mix in the sample volume are 3.72% and 88.35%, respectively.

Returning to the flow of the fluids through the system 100, after flowing through the instrumentation that includes the conductivity sensor 118, the first flowmeter 108 and the pressure sensor 120, and the first flowmeter 108, the HF mix and $iC_4$ stream, respectively, are then mixed again and flowed through valve 128 to the process return point 130. By continuously measuring a mass flow rate of $iC_4$ through the second flowmeter 106, the computer system 124 can also implement a mass balance calculation to ensure a balanced separation of the HF mix and the $iC_4$ (i.e., a separation in which the combined mass through the first flowmeter and the third flowmeter is equal, on average, to the mass through the second flowmeter). In addition, the computer system 124 can cross-calibrate the first, second, and third flowmeters to ensure that density and mass flowrate measurements are accurate.

In some systems, the $iC_4$ may be estimated to account for 6% of the sample volume sampled from the process sample point 102. However, the proportion of $iC_4$ in the sample volume may vary and may not always be 6%. Using the techniques described below, the system 100 can calculate, rather than estimate or assume, the proportion of $iC_4$. Based on the calculation of $iC_4$, concentration, the system 100 can determine the percentage concentrations of the components of the HF mix in the sample volume. Furthermore, by implementing a dynamic response control system, the noise in the readings of the instrumentation can, in some cases, be decreased. Consequently, the system 100 can be implemented to control and optimize concentrations of the components of the HF mix in the sample volume.

The instrumentation shown in FIG. 1 (first, second, and third flowmeters 108, 106, 110, conductivity sensor and transmitter 118, pressure sensor and transmitter 120) are connected to the computer system 124. For example, the computer system 124 can include one or more computers or processors. In some implementations, the instrumentation transmits values of measured parameters to the computer system 124. For example, the second flowmeter 106 transmits density, mass flow rate, and volumetric flow rate values to the computer system 124. The computer system 124 can include a computer storage medium to store the values received from the instrumentation. The computer system 124 also includes a computer-readable medium storing computer software instructions executable by data processing apparatus to perform calculations related to mass balance, volumetric flow balance, and calculations to determine density, conductivity and concentration.

In addition, the computer system 124 is coupled to the valves (the first valve 122, the second valve 116, the 3-way valve 112) to transmit instructions and control a state of each valve. For example, in response to receiving mass flow rate measurements from the flowmeters 106, 108, and 110, the computer system 124 can determine a level by which the first valve 122 should be opened (or closed). The computer system 124 can transmit a signal to open (or close) the first valve 122 by that level. In some implementations, the computer system 124 can transmit a signal to entirely open or entirely close a valve. Alternatively, the computer system 124 can transmit a signal to partially open or partially close a valve. Strength of the signal that the computer system 124 transmits can correspond to a level to which the valve is to be opened or closed. The computer system 124 may implement a control system such as a proportional-integral-derivative (PID) control loop to control the position of the valve, for example, based on the mass flow rate measurements from the flowmeters 106, 108, and 110 according to the parameters described further below.

The density reading of the second flowmeter 106, which is exposed to the complete sample volume from process sample point 102, varies with the proportion of $iC_4$ in the sample volume. However, the presence of two immiscible fluids (HF mix and $iC_4$) may not induce any bias errors into the readings. On average, the density and mass flow readings generated by the second flowmeter 106 match the true mean values of the sample volume. In particular, if the mass flow and density readings are taken over an averaging period, then the averaged mass flow and density values can be considered as being sufficiently representative of the sample volume. In some implementations, the averaging period can be, for example, 1 minute or 5 minutes or 10 minutes, where the measurement update from each instrument can be of the order of 1 second. The selection of the averaging period can vary between different systems or within the same system. The averaging period can be selected by, for example, monitoring the standard deviation of the density time series. A short averaging period can provide a good dynamic response to changes in the $iC_4$ content, while providing stable readings for the mass balance calculation described below.

According to industrial knowledge, the percentage by volume of $iC_4$, as a proportion of the sample volume, is estimated to be 6%. If the actual percentage by volume of $iC_4$, in the sample volume matches the estimate and that the system 100 is operating in an entirely balanced way, i.e., the volume of $iC_4$ in the separation vessel 114 is also 6%. If the first valve 122 were closed completely and the second valve 116 were open, the proportion of $iC_4$ in the separation vessel 114 will steadily increase because the HF mix will escape through the second valve 116 whereas the $iC_4$, that has risen to the top region of the separation vessel 114, will not. In this scenario, because the liquids are incompressible and there are no gasses present in the system, the volumetric flow rates are balanced. In other words:

$$Q_2\text{(volumetric flow rate through second flowmeter)}= Q_1+Q_3$$

The computer system 124 can calculate $Q_i$ for each flowmeter by receiving mass flow rate and density readings from the flowmeter. When the first valve 122 is closed:

$$Q_3=0; Q_2=Q_1$$

With reference to the mass flow balance in this scenario, because the separation vessel 114 is large, when the first valve 122 is closed, the vessel 114 begins to accumulate more $iC_4$. However, until it is effectively full of $iC_4$, the vessel 114 still manages to filter the $iC_4$ out from the stream passing through the first flowmeter 108. This is achieved by substituting the equivalent volume of high density HF for low density $iC_4$ in the stream sent to the first flowmeter 108, through the action of buoyancy in the separating vessel. Consequently:

$$M_2\text{(mass flow rate through second flowmeter)}<M_1+M_3$$

The computer system 124 can receive mass flow rate readings from each flowmeter. When valve 1 is shut, $M_3$ is 0.

Thus, although the volumetric flow rate through the second flowmeter 106 is equal to the sum of the volumetric flow rates through the first flowmeter 108 and the third flowmeter 110, a mass flow imbalance exists because the sample volume that flows through the second flowmeter 106 contains low density $iC_4$ while the sample volume that flows through the first flowmeter 108 is pure high density HF mix. In some implementations, the mass flow comparison can be performed over the averaging period described above.

Further, the imbalance is temporary, i.e., until the separation vessel 114 is effectively full of $iC_4$. At that time the first flowmeter 108 will receive a combination of HF mix and $iC_4$, and the mass balance will (on average) be restored. In addition, the imbalance that will be created even when the first valve 122 is completely closed will be small. With 6% $iC_4$ in the sample stream, and assuming densities of 600 kg/m³ and 1000 kg/m³ for $iC_4$ and HF mix, respectively, the mass flow difference between $M_2$ and $(M_1+M_3)$ will be 2.4%.

In another scenario, if the second valve 116 were closed and the first valve 122 were fully open, then:

$$Q_1=0; M_1=0$$

Because all of the sample volume will flow through the third flowmeter 110:

$$Q_2=Q_3$$

The top region of the separation vessel 114 includes $iC_4$ only. Thus, initially, only $iC_4$ flows through the third flowmeter 110. Consequently:

$$M_2 > M_1 + M_3$$

Mass balance will be restored when the layer of $iC_4$ at the top region of the separation vessel 114 is exhausted. When the first valve 122 is fully open, if the second valve 116 is assumed to also be open (rather than entirely closed), more $iC_4$, for example, twice the nominal flowrate of $iC_4$, will be allowed through the third flowmeter 110. In other words, whereas the volume of $iC_4$ flowing through the third flowmeter 110 would contain 6% $iC_4$ by volume when the second valve 116 is fully open, the level by which the second valve 116 is open causes the volume of $iC_4$ to be 12%. In this scenario also, $$M_2 > M_1 + M_3$$

In sum, if the first valve 122 is maintained at an optimum open level, then a mass flow imbalance between the mass flow rate through the second flowmeter 106 and the first and third flowmeters (108 and 110, respectively) can be decreased or eliminated. If the first valve (122) is less open than the optimum open level, then the second flowmeter 106 measures less mass flow than the first and second flowmeters (108 and 110, respectively) combined. Conversely, if the first valve 122 is more open than the optimum open level, then the second flowmeter 106 measures more mass flow than the first and third flowmeters (108 and 110, respectively) combined.

The first valve 122 can remain open at a level sufficient to ensure that all of the $iC_4$ in the sample volume is separated to the top region of the separation vessel 114 and that no $iC_4$ enters the conductivity sensor and transmitter 118, the first flowmeter 108, and pressure sensor and transmitter 120, that measure the concentrations of HF, water, and ASO in the $iC_4$-free HF mix. In some situations, the separation vessel 114 can have so large a capacity that changes in the $iC_4$ mass flow rate (and hence its proportion in the sample volume) are masked. In such situations, a change in the $iC_4$ may not be observed in the third flowmeter 110 unless the position of the first valve 110 is adjusted. Because the aforementioned mass imbalance is related to a level at which the valve 110 is open, the system 100 can detect and adjust for changes in the proportion of $iC_4$ using the control features of the computer system 124. To do so, the computer system 124 can execute computer software instructions stored on the computer-readable medium to perform the following function:

If $M2<M1+M3$, open valve 1 (122) further;

If $M2>M1+M3$, close valve 1 (122) further.

For example, flow control can be implemented as a PID control loop designed to maintain the value of $[M_2-(M_1+M_3)]$ at a set point of zero. By performing the aforementioned operations, the system 100 can facilitate a balanced separation of the HF mix and $iC_4$ stream, so that the third flowmeter 110 will respond rapidly and accurately with changes in the flow rate of $iC_4$ in the sample stream.

An example of pseudo-code executed by the computer system 124 to determine the concentration of $iC_4$ in the sample stream is described below. The following variables are defined in the pseudocode:

| Variable | Definition |
| --- | --- |
| T | number of seconds between samples from Coriolis meters (for example 1 s) |
| K | number of samples in averaging period (for example 60) |
| I | sample counter |
| M1 | Mass flow rate from Mass Flow Meter 1, updated every T seconds, in kg/s. |
| D1 | Density reading from Mass Flow Meter 1, updated every T seconds, in kg/m3. |
| M2, M3, D2, D2 | As above for Mass Flow Meter 2 and 3 |
| Q1 | Volumetric Flow from Mass Flow Meter 1 derived from M1 and D1, in liters/s. |
| Q2, Q3 | As above for Mass Flow Meter 2 and 3 |
| isoB_V | Percentage of isobutene by Volume, % |
| M1_sum | M1 accumulated over K samples to collect samples |
| M2_sum, M3_sum | As above for Mass Flow Meter 2 and 3 |
| M1_av | M1 averaged over K samples |
| M2_av, M3_av | As above for Mass Flow Meter 2 and 3 |
| Q1_sum | Q1 accumulated over K samples to collect samples |
| Q2_sum, Q3_sum | As above for Mass Flow Meter 2 and 3 |
| Q1_av | Q1 averaged over K samples |
| Q2_av, Q3_av | As above for Mass Flow Meter 2 and 3 |
| MB | Mass Balance, kg/s, based on averaged data |
| MBP | Mass Balance Percentage, % |
| QB | Volume Balance, 1/s, based on averaged data |
| QBP | Volume Balance Percentage, % |

Initialisation: I = 0; M1_sum = 0; M2_sum = 0; M3_sum = 0; Q1_sum = 0; Q2_sum = 0; Q3_sum = 0;
Operation:
While (true) /* loop forever */
1. I + I + 1;
2. Collect M1, D1, M2, D2, M3, D3 from Coriolis Mass Flow Meters 1,2,3;
3. Q1 = 1000 * M1/D1;
4. Q2 = 1000 * M2/D2;
5. Q3 = 1000 * M3/D3;
6. Iso_BV = 100* Q3/(Q1 + Q3)
7. M1_sum = M1_sum + M1
8. M2_sum = M2_sum + M2
9. M3_sum = M3_sum + M3
10. Q1_sum = Q1_sum + Q1
11. Q2_sum = Q2_sum + Q2
12. Q3_sum = Q3_sum + Q3
13. Display/Record M1, D1, Q1, M2, D2, Q2, M3, D3, Q3, Iso_BV.
14. If I == K /* do average calculations and flow control */
   a. M1_ave = M1_sum/K
   b. M2_ave = M2_sum/K
   c. M3_ave = M3_sum/K
   d. MB = M1_ave + M3_ave − M2_ave
   e. MBP = MB/M2_ave
   f. Adjust valve position using PI controller with target MBP = 0
   g. Q1_ave = Q1_sum/K
   h. Q2_ave = Q2_sum/K
   i. Q3_ave = Q3_sum/K
   j. QB = Q1_ave + Q3_ave − Q2_ave /* Volumetric Balance as Diagnostic */
   k. QBP = QB/Q2_ave
   l. Display MB, MBP, valve position, QB, QBP
   m. I = 0; M1_sum = 0; M2_sum = 0; M3_sum = 0; Q1_sum = 0; Q2_sum = 0; Q3_sum = 0; /* reset totals*/
15. End /* I == K */

The proportion of $iC_4$ in the sample stream is given by mass as follows:

% iso-butane by mass = 100% * $M_3$ / ($M_1 + M_3$), and by volume as follows:

% iso-butane by volume = 100% * $Q_3$ / ($Q_1 + Q_3$)

The readings from the first and third flowmeters (108 and 110, respectively) are used for this calculation as they will have reduced noise compared with the readings from the second flowmeter 106.

Once the mass flow of $iC_4$ through the third flowmeter 110 is controlled by opening and closing the first valve 122, as described above, the concentrations of the components of the HF mix can be determined from the volume of HF mix that flows from the separation vessel 114 through the second valve 116 through the conductivity sensor and transmitter 118, the first flowmeter 108, and the pressure sensor and transmitter 120. When other trace components of the HF mix are neglected, the HF mix can be approximated to be a ternary solution, which can be modeled as a 3-component system consisting of HF, water, and ASO. The concentrations of the components of a ternary solution can be determined by determining the concentrations of two of its components and inferring the third as a remainder to make up a total of 100%. A two-component solution (i.e., a binary solution) can be characterized by obtaining a density measurement of one component. The density of the component should vary uniquely with solution composition because determination of one component allows the other to be inferred as the remainder to make up a total of 100%. Analogously, a ternary solution can be characterized by two density measurements, as long as each of the two density measurements varies uniquely with the respective concentration of the component.

Electrolytic conductivity sensors can be used to determine a concentration of water in HF. Water dissolves in undergoing the following dissociation reaction:

$$2HF + H_2O \rightarrow HF_2^- + H_3O^+.$$

The dissolution products are ionized species, which makes the solution conductive. In binary HF/water solutions, the concentration of conductive species and therefore the conductivity is determined by the water concentration. The third major component of the HF mix, i.e., ASO, dissolves without the creation of ions. Consequently, a conductivity measurement is an uncompromised predictor of water concentration in the reaction mixture.

In some implementations, the conductivity sensor and transmitter 118 can be an electrodeless, non-contacting conductivity sensor. The sensor 118 can include a bore of inert material, for example, a pipe, through which the HF mix can pass. External to the bore, a coil called a "drive toroid" can generate an oscillating magnetic field, which induces an alternating current in the HF mix. The current, in turn, can generate an oscillating signal in a second external coil called a "sense toroid." The signal in the sense toroid, which is proportional to HF mix fluid conductivity, can be transmitted to the computer system 124. Because the fluid conductivity is proportional to the water concentration, the computer system 124 can be executed to calculate water concentration based on the received signal.

Once the concentration of water in the HF mix has been measured, a second measurement, i.e., of density, can be used to determine the HF and ASO concentrations, as described below. Light hydrocarbons have densities as low as 0.6 g/cc, whereas the density of pure HF is nearly 1.0 g/cc (almost the same density as water). Thus, the relative concentrations of HF and ASO affect the density of the alkylation mixture while water does not. Consequently, density can be used to determine the composition of either HF or ASO in the HF mix.

In some implementations, the first flowmeter 108 and the pressure sensor and transmitter 120 can be implemented as a Coriolis sensor which measures both density and mass flow rate. A Coriolis sensor is a coiled tube on which a resonant vibration is induced. The system 100 can determine mass flow and density by analysis of phase shift and frequency of the tube vibration, respectively. As with conductivity, the HF mix passes through a simple pipe shaped as a coil. With two measurements—conductivity and density—two components of the HF mix are determined, and the third is the remainder.

Knowing the concentration of water from the conductivity measurement and the concentration of HF or ASO from the density measurement, the concentration of the third component is simply the remainder because:

% HF+% ASO+% Water=100%

In some alternative situations, temperature and a second-order influence of interactions that may occur between the ASO and water may affect the conductivity and density measurements. All species in a solution affect each other directly or indirectly. In such situations, corrections for temperature and interactions between the components of the HF mix can be built into the system 100. To do so, a chemometric model can be developed for recording conductivity (cond), flow, pressure (P), density (ρ), and temperature (T) of HF mix. The data gathered from the system can be time-correlated to % HF, % water, and % ASO over a time period, for example, four months. By implementing statistical techniques (for example, multivariate regression), the data can be fit to equations that predict % water and % HF as functions of conductivity, density, and temperature. In equation form:

% water=$f_1$(cond)+$f_1$(ρ)+$f_1$(T)

% HF=$f_2$(cond)+$f_2$(ρ)+$f_2$(T)

Then,

% ASO=100−% HF−% water

In an alternative situation, the system 100 can be implemented to determine concentrations of components of the sample volume without implementing a control feedback loop, as described previously. In such situations, the fluid that exits the separation vessel 114 and flow through the third flowmeter 110 through the first valve 122 may not be pure $iC_4$ but may include some HF mix. Such a situation may arise because of one or more of several reasons. For example, it may not be practical to implement control of the first valve 122. The separation process in the separation vessel 114 may only be partial. The slugging of HF and $iC_4$ in the sample volume may cause some HF to flow through the third flowmeter 110.

In such situations, the concentrations of the components of the sample volume can be determined by placing the first valve 122 in a fixed position. For example, the first valve 122 is fixed such that approximately half of the total flow that flows through the second flowmeter 106 passes through the first flowmeter 108. Notably, the fluid that flows through the first flowmeter 108 is pure HF mix because the $iC_4$ has been separated from the HF mix in the separation vessel 114. Thus, the first flowmeter 108 receives pure HF mix, and both the second flowmeter 106 and the third flowmeter 108 receive a mixture of HF mix and $iC_4$. Because each of the first and third flowmeters (108, 110) receive half the sample volume relative to the second flowmeter 106, and because the third flowmeter 110 receives all the $iC_4$ and the first flowmeter 108 receives no $iC_4$, density readings by the flowmeters will be different from each other. Using the techniques described below, this difference can be used to determine the proportion of $iC_4$ by mass and volume.

The computer system 124 can receive readings measured by the flowmeters and determine average readings over averaging periods. The averaging periods can be selected to ensure that short-term variations in the HF mix to $iC_4$ proportions average out. The computer system 124 can determine the concentrations of the components of the sample volume based on an assumption that a density of $iC_4$ is 593.4 kg/m$^3$.

An example of calculations executed by the computer system 124 to determine the concentration of $iC_4$ in the sample stream in the alternative implementation is described below. The following variables are defined in the pseudocode:

| Variable | Definition |
|---|---|
| T | number of seconds between samples from Coriolis meters (for example 1 s) |
| K | number of samples in averaging period (for example, 60) |
| I | sample counter |
| M1 | Mass flow rate from Mass Flow Meter 1, updated every T seconds, in kg/s. |
| D1 | Density reading from Mass Flow Meter 1, updated every T seconds, in kg/m3. |
| M2, M3, D2, D2 | As above for Mass Flow Meter 2 and 3 |
| Q1 | Volumetric Flow from Mass Flow Meter 1 derived from M1 and D1, in liters/s. |
| Q2, Q3 | As above for Mass Flow Meter 2 and 3 |
| isoB_V | Percentage of isobutene by Volume, % |
| M1_sum | M1 accumulated over K samples to collect samples |
| M2_sum, M3_sum | As above for Mass Flow Meter 2 and 3 |
| M1_av | M1 averaged over K samples |
| M2_av, M3_av | As above for Mass Flow Meter 2 and 3 |
| Q1_sum | Q1 accumulated over K samples to collect samples |
| Q2_sum, Q3_sum | As above for Mass Flow Meter 2 and 3 |
| Q1_av | Q1 averaged over K samples |
| Q2_av, Q3_av | As above for Mass Flow Meter 2 and 3 |
| D_iC4 | Density of iC$_4$ (assumed 593.4 kg/m$^3$) |
| D_HF | Calculated density of HF mix |
| V_iC4 | Calculated volumetric flow rate of iC$_4$ |
| V_HF | Calculated volumetric flow rate of HF mix |

Variables M1, D1, M2, D2, M3, and D3 are measured by the first, second, and third flowmeters, respectively. The computer system 124 determines corresponding time averages for the measurements, for example, by executing the pseudocode described above. The computer system 124 than calculates the density of the HF mix and volumetric flow rates of iC$_4$ and HF mix as follows.

The volumetric and mass flow rates through the flowmeters should balance. In other words:

$$V2\_av=V1\_av+V3\_av \text{(expected volumetric balance)}$$

$$M2\_av=M1\_av+M3\_av \text{(expected mass flow balance)}$$

If the mass balance readings are noisy, but the mean is near zero (i.e., less than a threshold), then the averaging time can be increased to decrease the noise. If, however, the mean is greater than the threshold, then the flowmeters can be calibrated as described with reference to FIG. 3. Further, slip between the iC$_4$ and HF mix (for example, at low velocity flows) can cause density offsets.

The first flowmeter 108 sees pure HF mix. Consequently, the computer system 124 can update the density readings of the first flowmeter 108 each averaging period:

$$D\_HF=D1\_av$$

The second flowmeter 106 and the third flowmeter 110 see different proportions of HF mix and iC$_4$. The computer system 124 can calculate density differences for these two flowmeters as follows:

$$D2\_drop=[(D\_HF-D2\_av)/D\_HF] \times 100\% \text{(\% drop in density at } 2^{nd} \text{ flowmeter)}$$

$$D3\_drop=[(D\_HF-D3\_av)/D\_HF] \times 100\% \text{(\% drop in density at } 3^{rd} \text{ flowmeter)}$$

A K factor can be used to convert density drop into volumetric ratio for iC$_4$.

$$K\_factor=(D\_HF-D\_iC_4)/D\_HF \text{(density drop to volumetric ratio for } iC_4\text{)}$$

The computer system 124 can determine the volumetric proportion of iC$_4$ for the entire flow, based on the readings of the second flowmeter 106:

$$iC_4\_V=D2\_drop/K\_factor \text{(\% by volume of } iC_4 \text{ in fluid received by } 3^{rd} \text{ flowmeter)}$$

$$V\_iC_4=V2\_av \times iC_4\_V/100 \text{(volumetric flowrate of } iC_4 \text{ through } 2^{nd} \text{ flowmeter)}$$

The computer system 124 can implement a consistency check using the readings of the third flowmeter 110.

$$iC_4\_V\_check=D3\_drop/K\_factor \text{(\% volume of } iC_4 \text{ in fluid received by } 3^{rd} \text{ flowmeter)}$$

$$V\_iC_4\_check=V3\_av \times iC_4\_V\_check/100 \text{(volumetric flowrate of } iC_4 \text{ through } 3^{rd} \text{ flowmeter)}$$

The computer system 124 can check that V_iC$_4$=V_iC$_4$_check.

Having determined the concentration proportion of iC$_4$ in the sample volume, the computer system 124 can determine the concentration proportion of each of HF, water, and ASO in the HF mix, and also the concentration proportion of each of HF, water, and ASO in the sample volume using techniques described above with reference to FIG. 2A.

Figure 2A:
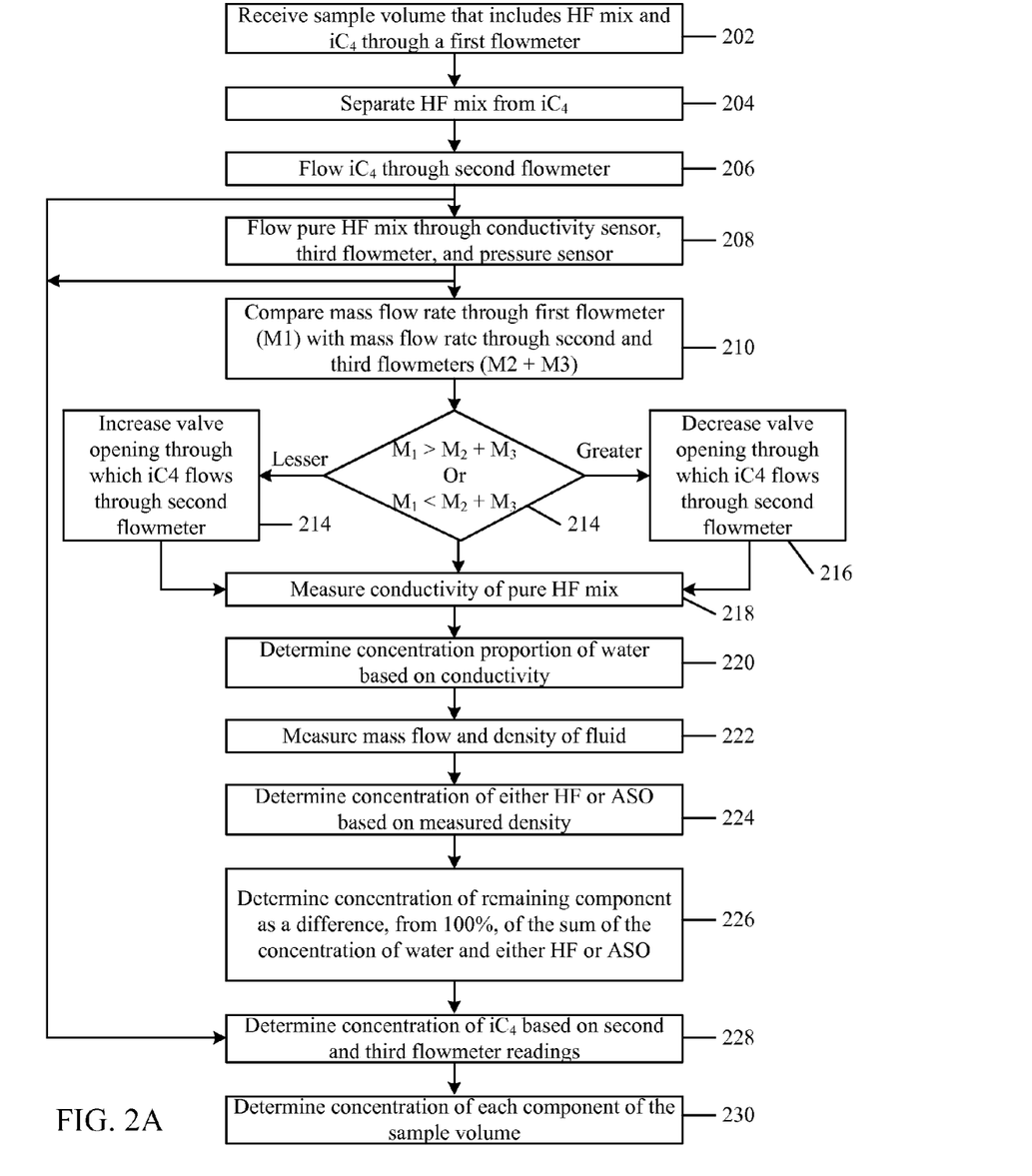
FIG. 2A is a flowchart of an example process for determining concentrations of components of a volume sampled from a process stream.

FIG. 2A is a flowchart of an example process 200 for determining concentrations of components of a volume sampled from a process stream. The sample volume that includes HF mix and iC$_4$ can be received through a first flowmeter (202). The HF mix can be separated from the iC$_4$ (204). The separation yields pure HF mix, which can be flowed through the conductivity sensor 118, the first flowmeter 108, and the pressure sensor 120 (206). The iC$_4$ can be flowed through the third flowmeter 110 (208). The mass flow rate through the second flowmeter 106 (M$_1$) can be compared with the mass flow rate through the first flowmeter 108 and the third flowmeter 110 (M$_2$+M$_3$) (210). It can be checked if M$_1$>M$_2$+M$_3$ or if M$_1$<M$_2$+M$_3$ (212). If lesser, then the opening of the valve through which iC$_4$ flows through the third flowmeter (110) can be increased further (214). If greater, then the valve opening can be decreased further (216) to maintain a balance in the mass of iC$_4$ through the third flowmeter 110. The conductivity of the pure HF mix can be measured (step 218), for example, by the conductivity sensor. The conductivity sensor can then transmit the measured conductivity to the computer system 124. The concentration proportion of water in the HF mix (i.e., percentage of water in the HF mix) can be determined based on the conductivity (2220), for example, by the computer system 124. Mass flow and density of the fluid can be measured (222), for example, by the first flowmeter 108. The concentration proportion of either HF or ASO (i.e., percentage of either HF or ASO in the HF mix) can be determined based on the measured density (224), for example, by the computer system 124 that receives the mass flow and density measurements from the first flowmeter 108. The concentration of the remaining component (i.e., percentage of either ASO or HF in the HF mix), can be determined as a difference, from 100%, of the sum of the concentration of water and either HF or ASO (226). The concentration proportion of iC$_4$ (for example, percentage of iC$_4$ in the sample volume) can be determined based on second and third flowmeter readings (228). The concentration proportion of each component of the sample volume can be determined based on the previously determined concentration proportions (230). For example, if the percentage of $iC_4$ in the sample volume was determined to be 7%, then the proportion of HF mix in the sample volume is 93% (100%-7%). If the percentage of water, HF, and ASO in the HF mix is 1%, 95%, and 4%, respectively, then the percentage of water, HF, and ASO in the sample volume is 0.93% (1% of 93%), 88.35% (95% of 93%), and 3.72% (4% of 93%), respectively.

Figure 2B:
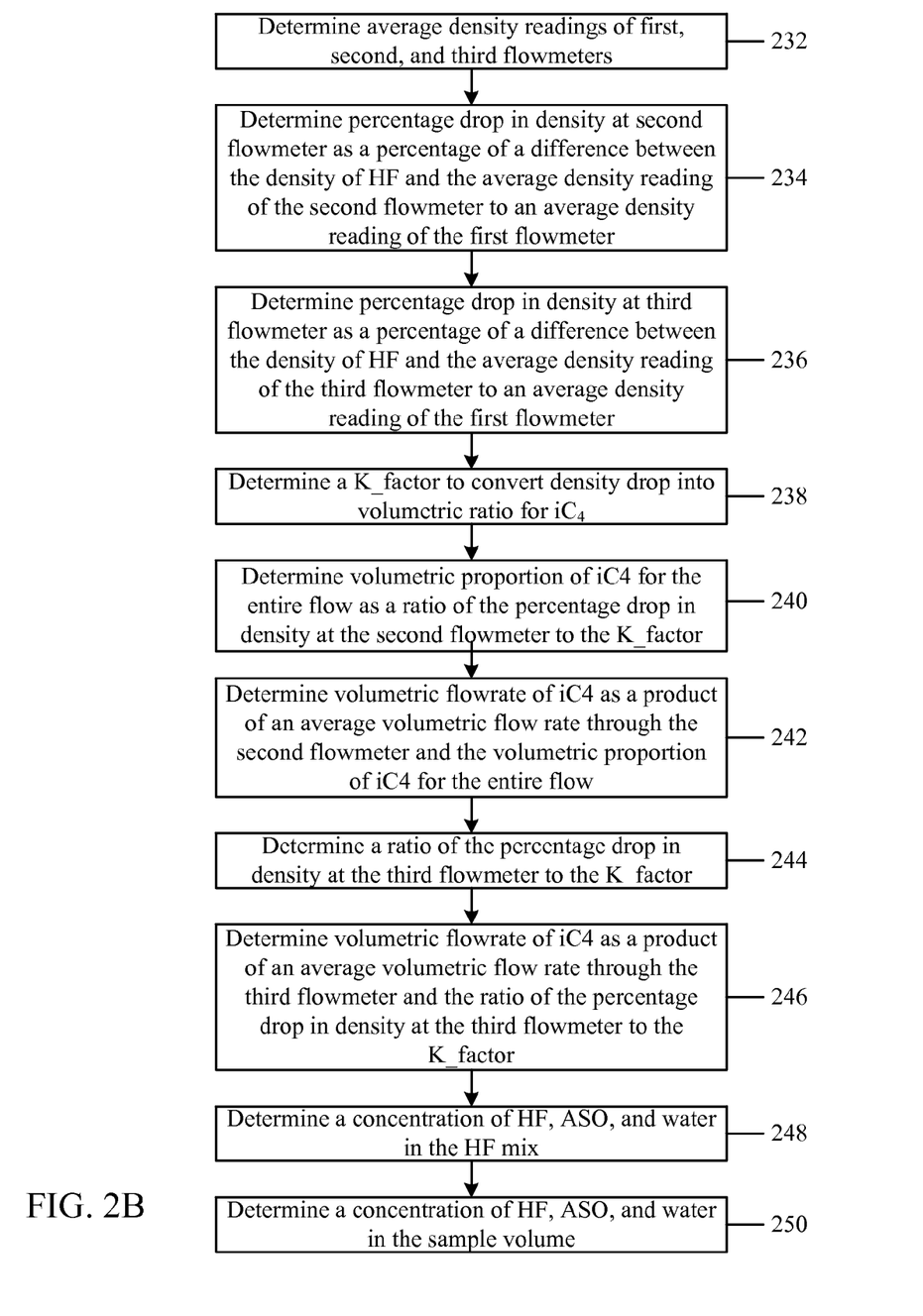
FIG. 2B is a flowchart of another example process for determining concentrations of components of a volume sampled from a process stream.

FIG. 2B is a flowchart of another example process for determining concentrations of components of a volume sampled from a process stream. The example process can be implemented, for example, by the computer system 124 and may be employed when valve control is not employed. Similarly to FIG. 2A, a sample volume that includes HF mix and $iC_4$ can be received through a first flowmeter. The HF mix and the $iC_4$ can be separated using the separation vessel. The pure HF mix can be flowed through the second flowmeter. The partially separated $iC_4$ that may include some HF mix can be flowed through the third flowmeter. Each of the first, second, and third flowmeters can take density and flow measurements on the received fluids, and transmit the measurements to the computer system 124.

Average density readings of first, second, and third flowmeters can be determined (232). A percentage drop in density at second flowmeter can be calculated as a percentage of a difference between the density of HF and the average density reading of the second flowmeter, to an average density reading of the first flowmeter (234). A percentage drop in density at third flowmeter can be determined as a percentage of a difference between the density of HF and the average density reading of the third flowmeter, to an average density reading of the first flowmeter (236). A K_factor can be determined to convert density drop into volumetric ratio for $iC_4$ (238). A volumetric proportion of $iC_4$ for the entire flow can be calculated as a ratio of the percentage drop in density at the second flowmeter to the K_factor (240). A volumetric flowrate of $iC_4$ as a product of average volumetric flow rate through the second flowmeter and the volumetric proportion of $iC_4$ for the entire flow can be determined (242). A ratio of the percentage drop in density at the third flowmeter to the K_factor can be calculated (244). A volumetric flowrate of $iC_4$ as a product of an average volumetric flow rate through the third flowmeter and the ratio of the percentage drop in density at the third flowmeter to the K_factor can be determined (246). To implement a consistency check, the volumetric flowrate calculated based on the volumetric proportion of $iC_4$ through the second flowmeter can be compared with the volumetric proportion of $iC_4$ through the third flowmeter. Similarly to the process described with reference to FIG. 2A, a concentration of HF, ASO, and water in the HF mix can be determined (248). A concentration of HF, ASO, and water in the sample volume can be determined based on the concentration of $iC_4$ in the sample volume and a concentration of HF, ASO, and water in the HF mix (250).

Figure 3:
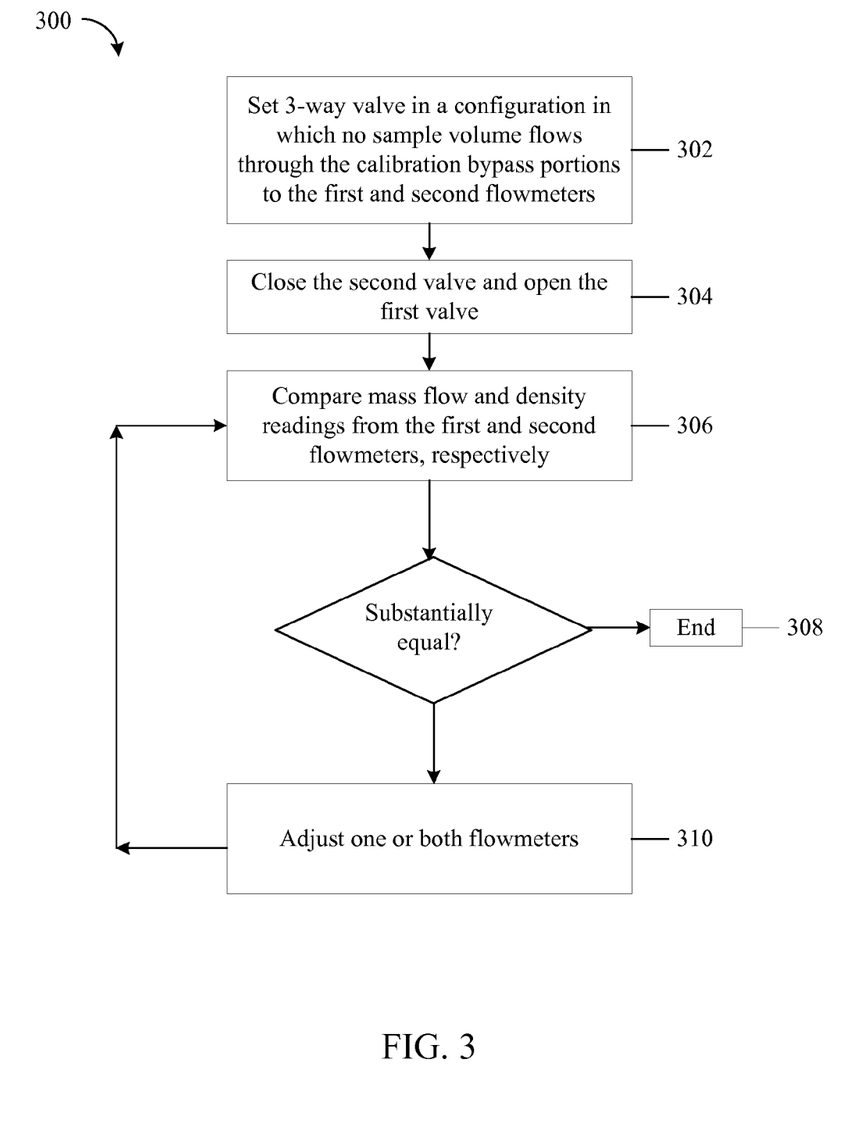
FIG. 3 is a flowchart of an example process for calibrating three flowmeters.

FIG. 3 is a flowchart of an example process 300 for calibrating three flowmeters. In some implementations, the system 100 can cross-calibrate the first, second, and third flowmeters (106, 108, and 110, respectively) to ensure an accurate determination of the flow rate of $iC_4$. Cross-calibration can decrease or eliminate offsets between the readings of the three flowmeters to ensure that a correct mass balance calculation is achieved. To cross-calibrate the flowmeters, the 3-way valve 112 can be set in a second configuration in which no sample volume flows to the separation vessel 114; instead, the sample volumes flow through calibration bypass portion 1 and calibration bypass portion 2 to the first flowmeter 108 and the second flowmeter 110, respectively (302). The 3-way valve 112 is an example of a valve arrangement to enable fluid flow in the first configuration (described above) and the second configuration. Another type of valve or multiple valves can be arranged to achieve a function that is equivalent to that of the 3-way valve 112.

With the 3-way valve 112 set in the second configuration, the second valve 116 can be closed and the first valve 122 can be opened such that all of the sample volume flows first through the second flowmeter 106 and then through the third flowmeter 110 (304). The two flowmeters can transmit mass flow and density readings to the computer system 124. The computer system 124 can average the readings over the averaging period, and compare (306) the readings. It can be checked if the two readings are substantially equal to each other. For example, two readings are substantially equal to each other if the difference between the two readings satisfies a threshold, such as within 0.2% of the reading. If so, then the process 300 ends (308) as the two flowmeters are calibrated. If not, then this indicates that the flowmeters are not calibrated. The flowmeters can then be adjusted (310) and the comparison can be repeated. Similarly, the first and second flowmeters (108 and 106, respectively) can be cross-calibrated by setting the 3-way valve 112 in the second configuration, closing the first valve 122 and opening the second valve 116. In addition to calibrating the flowmeters by comparing mass flow and density readings, calibration based on volumetric flow rates can also be performed. Specifically, when the 3-way valve 112 is in the second configuration and both the first valve 116 and the second valve 122 are open, then the volumetric flow rate through the second flowmeter 106 should be equal to the sum of the volumetric flow rates through the first flowmeter 108 and through the third flowmeter 110.

Examples of flowmeters that can be implemented in system 100, are described below. Types of flowmeters include digital flowmeters. For example, U.S. Pat. No. 6,311,136, which is hereby incorporated herein by reference, discloses the use of a digital flowmeter and related technology including signal processing and measurement techniques. Such digital flowmeters may be very precise in their measurements, with little or negligible noise, and may be capable of enabling a wide range of positive and negative gains at the driver circuitry for driving the conduit. Such digital flowmeters are thus advantageous in a variety of settings. For example, commonly-assigned U.S. Pat. No. 6,505,519, which is incorporated herein by reference, discloses the use of a wide gain range, and/or the use of negative gain, to prevent stalling and to more accurately exercise control of the flowtube, even during difficult conditions such as two-phase flow (for example, a flow containing a mixture of liquid and gas).

Although digital flowmeters are specifically discussed below, it should be understood that analog flowmeters also exist. Although such analog flowmeters may be prone to typical shortcomings of analog circuitry, for example, low precision and high noise measurements relative to digital flowmeters, they also may be compatible with the various techniques and implementations discussed herein.

Implementations of the computer system 124 and the operations described with reference to the computer system 124 can be implemented in digital electronic circuitry, or in computer software, firmware, or hardware, including the structures disclosed in this specification and their structural equivalents, or in combinations of one or more of them. Implementations of the computer system 124 can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, for example, a machine-generated electrical, optical, or electromagnetic signal, that is generated to encode information for transmission to suitable receiver apparatus for execution by a data processing apparatus. The computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (for example, multiple CDs, disks, or other storage devices).

The operations described in this specification can be implemented as operations performed by the data processing apparatus 124 on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, for example, an FPGA (field programmable gate array) or an ASIC (application-specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (for example, a universal serial bus (USB) flash drive), to name just a few. Devices suitable for storing computer program instructions and data include all forms of non-volatile memory, media and memory devices, including by way of example semiconductor memory devices, for example, EPROM, EEPROM, and flash memory devices; magnetic disks, for example, internal hard disks or removable disks; magneto-optical disks; and CD-ROM and DVD-ROM disks. The processor and the memory can be supplemented by, or incorporated in, special purpose logic circuitry.

To provide for interaction with a user, implementations of the computer system 124 can include a display device, for example, a CRT (cathode ray tube) or LCD (liquid crystal display) monitor, for displaying information to the user and a keyboard and a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A system to determine concentrations of components of a multiphase fluid, the system comprising:
    a first flowmeter configured to receive a fluid flow and to generate one or more measurements of the fluid flow, the fluid flow including a first liquid and a second liquid, wherein the first and second liquids are immiscible;
    a separation vessel configured to receive the fluid flow, and to at least partially separate the first liquid and the second liquid;
    a second flowmeter configured to receive either the second liquid or a mixture of the first liquid and the second liquid, through a valve and to generate one or more measurements of either the second liquid or the mixture of the first liquid and the second liquid, wherein a proportion of the second liquid to the first liquid in the mixture is greater than a proportion of the second liquid to the first liquid in the fluid flow;
    a third flowmeter configured to receive the first liquid and to generate one or more measurements of the first liquid; and
    a data processing apparatus operatively coupled to the first flowmeter, the second flowmeter, the third flowmeter, the data processing apparatus configured to perform operations comprising:
        receiving the one or more measurements of the fluid flow from the first flowmeter;
        receiving the one or more measurements of the second liquid or the mixture of the first liquid and the second liquid from the second flowmeter;
        receiving the one or more measurements of the first liquid from the third flowmeter, and
        determining a concentration of the second liquid in the fluid flow.

2. The system of claim 1, wherein the first liquid includes a first component, a second component, and a third component, and wherein the operations further comprise determining a concentration of each of the first component, the second component, and the third component in the first liquid.

3. The system of claim 2, wherein the operations further comprise determining a concentration of each of the first component, the second component, and the third component in the fluid flow based on the concentration of each of the first component, the second component, and the third component in the first liquid and the concentration of the second liquid in the fluid flow.

4. A system to determine concentrations of components of a four-component multiphase fluid, the system comprising:
    a first flowmeter configured to receive a fluid flow and to generate one or more measurements of the fluid flow, the fluid flow including a first component, a second component, a third component, and a fourth component;
    a separation vessel configured to receive the fluid flow, and to separate the fluid flow into a first mixture that includes the first, second, and third components and a second mixture that includes the fourth component;
    a second flowmeter configured to receive the second mixture through a valve and to generate one or more measurements of the second mixture;
    a third flowmeter configured to receive the first mixture and to generate one or more measurements of the first mixture; and
    a data processing apparatus operatively coupled to the first flowmeter, the second flowmeter, the third flowmeter, the data processing apparatus configured to perform operations comprising:
        receiving the one or more measurements of the fluid flow from the first flowmeter;
        receiving the one or more measurements of the second mixture from the second flowmeter;
        receiving the one or more measurements of the first mixture from the third flowmeter, and
        determining a concentration the fourth component in the fluid flow.

5. The system of claim 4, wherein the operations further comprise controlling, based on the measurements received from the first, second, and third flowmeters, a level by which the valve is open to maintain a mass balance between the first, second, and third flowmeters.

6. The system of claim 4, wherein the operations further comprise determining a concentration of each of the first component, the second component, and the third component in the first mixture.

7. The system of claim 6, wherein the operations further comprise determining a concentration of each of the first component, the second component, and the third component in the fluid based on the concentration of the fourth component in the fluid and the concentration of each of the first component, the second component, and the third component in the first mixture.

8. An acid catalyst analyzer system comprising:
    a first flowmeter configured to receive a sample volume that includes an acid catalyst mix and a hydrocarbon fluid, the acid catalyst mix including an acid, water, and acid soluble oils (ASO);
    a separation vessel configured to receive the sample volume from the first flowmeter, and to separate the acid catalyst mix from the hydrocarbon fluid;
    a second flowmeter adapted to receive the hydrocarbon fluid that has been separated from the acid catalyst mix, through a first valve;
    a third flowmeter adapted to receive the acid catalyst mix that has been separated from the hydrocarbon fluid through a second valve; and
    data processing apparatus operatively coupled to the first flowmeter, the second flowmeter, and the third flowmeter, the data processing apparatus configured to execute computer software instructions stored on a computer-readable medium to perform operations comprising:
        receiving a first set of mass flow and density readings, a second set of mass flow and density readings, and a third set of mass flow and density readings from the first flowmeter, the second flowmeter, and the third flowmeter, respectively,
        determining a concentration of the hydrocarbon fluid in the sample volume, and
        transmitting a signal to control a level by which the first valve is open to maintain a mass balance between the first flowmeter, and the second and the third flowmeters.

9. The system of claim 8, the operations further comprising:
  determining a first mass flow through the first flowmeter based on the first set of mass flow and density readings;
  determining a second mass flow through the second flowmeter based on the second set of mass flow and density readings;
  determining a third mass flow through the third flowmeter based on the third set of mass flow and density readings;
  comparing the first mass flow to a sum of the second mass flow and the third mass flow;
  upon determining that the first mass flow is less than the sum, increasing the level by which the first valve is open, or
  upon determining that the first mass flow is greater than the sum, decreasing the level by which the first valve is open.

10. The system of claim 8, further comprising a conductivity sensor coupled to the third flowmeter to receive the acid catalyst mix that has been separated from the hydrocarbon fluid, the conductivity sensor configured to measure a conductivity of the acid catalyst mix, wherein the conductivity sensor is operatively coupled to the data processing apparatus to transmit the measured conductivity to the data processing apparatus.

11. The system of claim 8, further comprising a pressure sensor coupled to the third flowmeter to receive the acid catalyst mix that has been separated from the hydrocarbon fluid, the pressure sensor configured to measure a pressure of the acid catalyst mix, wherein the pressure sensor is operatively coupled to the data processing apparatus to transmit the measured pressure to the data processing apparatus.

12. The system of claim 11, the operations further comprising:
  determining a concentration of the water in the acid catalyst mix based on the received conductivity, wherein the concentration of the water is proportional to the measured conductivity;
  determining a concentration of the acid in the acid catalyst mix based on the received third set of mass flow and density readings from the third flowmeter, wherein the concentration of the acid is proportional to the density readings in the third set; and
  determining a concentration of the ASO as a remainder of a sum of the concentration of the water and the concentration of the acid from 100%.

13. The system of claim 12, the operations further comprising determining the concentration of each of the water, the acid, and the ASO in the sample volume based on the concentration of the hydrocarbon fluid in the sample volume and the concentration of each of the water, the acid, and the ASO in the acid catalyst mix.

14. The system of claim 8, wherein the acid is Hydrofluoric acid.

15. The system of claim 8, further comprising a valve coupled to the first flowmeter, the second flowmeter, and the third flowmeter, and configured to enable flow of the sample volume received by the first flowmeter to the second flowmeter only or the third flowmeter only or both flowmeters simultaneously.

16. The system of claim 15, wherein the valve is a 3-way valve.

17. The system of claim 8, wherein the separation vessel includes a first inlet to receive the sample volume, the separation vessel sized to separate the acid catalyst mix and the hydrocarbon fluid based on a difference in a density of the acid catalyst mix and a density of the hydrocarbon fluid.

18. The system of claim 8, wherein the first flowmeter is a Coriolis flowmeter using a bent tube.

19. The system of claim 8, wherein the second flowmeter is a Coriolis flowmeter using a straight tube.

20. A method to determine concentrations of components of a multiphase fluid, the method comprising:
  receiving a fluid flow including a first liquid and a second liquid, wherein the first and second liquids are immiscible
  generating one or more measurements of the fluid flow;
  at least partially separating the first liquid and the second liquid;
  receiving either the second liquid or a mixture of the first liquid and the second liquid, wherein a proportion of the second liquid to the first liquid in the mixture is greater than a proportion of the second liquid to the first liquid in the fluid flow;
  generating one or more measurements of either the second liquid or the mixture of the first liquid and the second liquid;
  receiving the first liquid;
  generating one or more measurements of the first liquid; and
  determining a concentration of the second liquid in the fluid flow based on the one or more measurements of the fluid flow, the one or more measurements of the second liquid or the mixture of the first liquid and the second liquid from the second flowmeter, and the one or more measurements of the first liquid.

21. The method of claim 20, wherein the first liquid includes a first component, a second component, and a third component, and wherein the method further comprises determining a concentration of each of the first component, the second component, and the third component in the first liquid.

22. The method of claim 21, wherein the method further comprises determining a concentration of each of the first component, the second component, and the third component in the fluid flow based on the concentration of each of the first component, the second component, and the third component in the first liquid and the concentration of the second liquid in the fluid flow.

23. A method to determine concentrations of components of a four-component multiphase fluid, the system comprising:
  receiving a fluid flow including a first component, a second component, a third component, and a fourth component;
  generating one or more measurements of the fluid flow;
  separating the fluid flow into a first mixture that includes the first, second, and third components and a second mixture that includes the fourth component;
  receiving the second mixture;
  generating one or more measurements of the second mixture;
  receiving the first mixture;
  generating one or more measurements of the first mixture; and
  determining a concentration the fourth component in the fluid flow based on the one or more measurements of the fluid flow, the one or more measurements of the second mixture, and the one or more measurements of the second mixture.

24. The method of claim 23, wherein the method further comprises controlling, based on the one or more measurements of the fluid flow, the one or more measurements of the second mixture, and the one or more measurements of the second mixture, a level of the first mixture to maintain a mass balance between the first mixture and the second mixture.

25. The method of claim 24, wherein the method further comprises determining a concentration of each of the first component, the second component, and the third component in the first mixture.

26. The method of claim 25, wherein the method further comprises determining a concentration of each of the first component, the second component, and the third component in the fluid based on the concentration of the fourth component in the fluid and the concentration of each of the first component, the second component, and the third component in the first mixture.

* * * * *

UNITED STATES PATENT AND TRADEMARK OFFICE
CERTIFICATE OF CORRECTION

| | | |
|---|---|---|
| PATENT NO. | : 8,726,722 B2 | Page 1 of 1 |
| APPLICATION NO. | : 13/302780 | |
| DATED | : May 20, 2014 | |
| INVENTOR(S) | : Manus P. Henry | |

It is certified that error appears in the above-identified patent and that said Letters Patent is hereby corrected as shown below:

In the Claims:

Column 19, Claim 11, Lines 26-27:

The system of claim 8, further comprising a pressure sensor coupled to the third flowmeter to receive the acid catalyst mix Should read The system of claim 10, further comprising a pressure sensor coupled to the third flowmeter to receive the acid catalyst mix Column 19, Claim 12, Lines 35-36:

determining a concentration of the water in the acid catalyst mix based on the received conductivity Should read determining a concentration of the water in the acid catalyst mix based on the measured conductivity

Column 20, Claim 23, Lines 43-44:

A method to determine concentrations of components of a four-component multiphase fluid, the system comprising:

Should read

A method to determine concentrations of components of a four-component multiphase fluid, the method comprising:

Signed and Sealed this
Seventh Day of October, 2014

Michelle K. Lee
*Deputy Director of the United States Patent and Trademark Office*